United States Patent
Butz et al.

(10) Patent No.: US 10,653,602 B2
(45) Date of Patent: *May 19, 2020

(54) FOAM BOOSTING SACCHARIDE BLEND

(71) Applicant: COAST SOUTHWEST, INC., Placentia, CA (US)

(72) Inventors: Shannon Smith Butz, Paso Robles, CA (US); Amit Patel, Euless, TX (US)

(73) Assignee: Coast Southwest Inc., Placentia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/040,077

(22) Filed: Jul. 19, 2018

(65) Prior Publication Data
US 2019/0380940 A1    Dec. 19, 2019

Related U.S. Application Data

(63) Continuation of application No. 15/427,371, filed on Feb. 8, 2017, now Pat. No. 10,052,274.
(Continued)

(51) Int. Cl.
*A61K 8/04* (2006.01)
*A61K 8/60* (2006.01)
(Continued)

(52) U.S. Cl.
CPC ............... *A61K 8/60* (2013.01); *A61K 8/046* (2013.01); *A61K 8/442* (2013.01); *A61Q 5/02* (2013.01); *A61Q 19/10* (2013.01); *C09K 8/38* (2013.01); *C11D 3/0094* (2013.01); *C11D 3/221* (2013.01); *A61K 2800/5922* (2013.01); *C09K 8/594* (2013.01); *C09K 8/94* (2013.01)

(58) Field of Classification Search
CPC ... A61K 8/04; A61K 8/60; A61Q 5/02; A61Q 19/10; C11D 3/0094; C11D 3/22; C11D 3/221
See application file for complete search history.

(56) References Cited

U.S. PATENT DOCUMENTS 3,338,665 A    8/1967   Silverman
3,898,159 A    8/1975   Okabe et al.
(Continued)

FOREIGN PATENT DOCUMENTS

CN    1863899         11/2006
EA    1661976 A1      5/2006
(Continued)

OTHER PUBLICATIONS

International Search Report and Written Opinion for PCT/IB2017/050687 dated May 22, 2017.
(Continued)

*Primary Examiner* — Brian P Mruk
(74) *Attorney, Agent, or Firm* — Norton Rose Fulbright US LLP

(57) ABSTRACT

Disclosed is a foam booster that is capable of producing or increasing the amount of foam in any given composition. The foam booster includes a saccharide blend having 30 wt. % to 50 wt. % of an aldohexose or mixture of aldohexoses, 20 wt. % to 55 wt. % of a ketohexose or mixture of ketohexoses; and 10 wt. % to 20 wt. % of a disaccharide or mixture of disaccharides.

19 Claims, 3 Drawing Sheets

Related U.S. Application Data

(60) Provisional application No. 62/293,259, filed on Feb. 9, 2016.

(51) Int. Cl.

| | |
|---|---|
| *A61Q 5/02* | (2006.01) |
| *A61Q 19/10* | (2006.01) |
| *C11D 3/22* | (2006.01) |
| *C11D 3/00* | (2006.01) |
| *C09K 8/38* | (2006.01) |
| *A61K 8/44* | (2006.01) |
| *C09K 8/594* | (2006.01) |
| *C09K 8/94* | (2006.01) |

(56) References Cited

U.S. PATENT DOCUMENTS

| | | |
|---|---|---|
| 3,988,438 A | 10/1976 | Weinstein |
| 3,998,761 A | 12/1976 | Gary et al. |
| 4,364,837 A | 12/1982 | Pader |
| 4,718,493 A | 1/1988 | Hill et al. |
| 5,507,970 A | 4/1996 | Ishikawa et al. |
| 5,888,951 A | 3/1999 | Gagnebien et al. |
| 6,454,787 B1 | 9/2002 | Maddalo et al. |
| 7,012,053 B1 | 3/2006 | Barnabas et al. |
| 8,211,449 B2 | 7/2012 | Aust et al. |
| 9,050,253 B2 | 6/2015 | Tamarkin et al. |
| 10,052,274 B2* | 8/2018 | Butz .................. C09K 8/38 |
| 2002/0132037 A1* | 9/2002 | Zhou .................. A23L 27/33 |
| | | 426/658 |
| 2009/0311406 A1 | 12/2009 | Tapfer et al. |
| 2010/0152089 A1 | 6/2010 | Wattebled et al. |

FOREIGN PATENT DOCUMENTS

| | | |
|---|---|---|
| JP | H07331281 | 12/1995 |
| WO | WO0024856 | 5/2000 |

OTHER PUBLICATIONS

Written Opinion issued in International Patent Application No. PCT/IB2017/050687, dated Jan. 16, 2018.

Office Action issued in corresponding Chinese application No. 2017800162046, dated Nov. 25, 2019.

* cited by examiner

FOAM BOOSTING SACCHARIDE BLEND

CROSS-REFERENCE TO RELATED APPLICATIONS

This application is a continuation of U.S. patent application Ser. No. 15/427,371, filed Feb. 8, 2017 (now issued as U.S. Pat. No. 10,052,274), which claims the benefit of priority of U.S. Provisional Patent Application No. 62/293,259, filed Feb. 9, 2016. The contents of the referenced applications are incorporated into the present application by reference.

BACKGROUND OF THE INVENTION

A. Field of the Invention

The present invention relates generally to the fields of foamable compositions. More particularly, it concerns a blend of saccharides that can be used as a foam booster or foam-enhancing agent to enhance the foaming capabilities of a given composition. The saccharide blend can include a combination of an aldohexose (e.g., glucose or dextrose or both), a ketohexose (e.g. fructose), and a disaccharide (e.g., maltose) in specified weight % ranges that can then be added to and enhance the foaming properties of any given composition.

B. Description of Related Art

Many industries and consumers desire foamable compositions, or composition that are capable of being foamed. For example, foamable compositions can be used to deliver and control the application of a given drug or cosmetic ingredient to skin (U.S. Pat. Nos. 6,454,787; 8,211,449; and 9,050,253). Foamable compositions can be used to fill voids or penetrate porous surfaces such as in solid propant delivery to assist in recovery of fluids from fractured formations (U.S. Pat. Nos. 6,454,787 and 4,718,493). Cleaning/extracting compositions can use foamable compositions to move undesired waste into a foam and away from the item being cleaned (U.S. Pat. No. 3,898,159). Foamable compositions can be used to capture gaseous waste so that it is not released into the atmosphere (U.S. Pat. No. 3,338,665). Further, consumers may prefer foaming products because of the foam texture. Also, consumers may desire foamable cleaning compositions because it implies to the consumer that the composition is cleaning, such as with shampoos, soaps, body washes, or toothpastes.

The foams produced by foamable compositions vary greatly, and not all foams are suitable for all applications. Foam characteristics that vary can include foaming power, foam quantity, foam stability, foam density, foam load capacity, foam texture, and the speed at which a foam is created. Further, some foams are more resilient to changes in the foaming agent or to the presence of agents that can modify the characteristics of a foam, such as anti-foaming agents. For example, some foamable compositions lose foaming power when a small or threshold amount of an anti-foaming agent is added to the composition. However, anti-foaming agents can include oils, fragrances, solids, etc., that are desired or necessary for the end use of the foamable composition.

In most cases, foamable compositions contain one or a mixture of surfactants that act as a foaming agents that enable the composition to form a foam. However, not every surfactant or foaming agent is suitable for all applications where a foam is desired or required. As an example, some foaming agents are irritants or toxic and are not suitable for cosmetic and pharmaceutical applications. Other foaming agents are not capable of providing foam stability for more than a few second, and some foaming agents cannot provide the required foam load capacity for certain applications. In some applications, suitable foaming agents and concentrations thereof can be limited, which also limits the foam characteristics possible for foamable compositions suitable for those applications.

To overcome these limitations, foam boosters (also referred to as foam-enablers or foam enhancers) can in some instances be added to a given foamable composition to modify the characteristics of the foam. There are several patents and applications that describe foam boosters or foam-enablers. For example, EP 1661976 A1 discloses ethercarboxylates and glycerine derivatives as foam-enhancing agents in aqueous compositions. U.S. Publication No. 2010/0152089 discloses a liquid cleaning agent having a foam booster that can be alkylaminocarboxylic acid salts, fatty acid amides, fatty acid alkanolamides, betaines, sulfobetaines, polymeric compounds, or mixtures thereof. These foam boosters can be expensive, cause skin irritation, and can be chemically reactive and prone to react with other ingredients in a given product formulation, thereby introducing instability into the formulation.

In some instances, attempts have been made to use saccharides in foamable compositions. For example, U.S. Pat. No. 4,364,837 discloses a shampoo composition that comprises about 15 to 70% by weight of a water-miscible saccharide. The presence of saccharide in the shampoo is taught to increase the foam quality at a given concentration of detergents, or to maintain the same level of foam quality at a lower detergent concentration. However, the concentration of saccharides in the shampoo is quite high, at about 15 to 70% by weight of the total weight of the composition, which can negatively affect the rheological and tactile properties of the composition. Still further, the patent explains that saccharide levels below 15 wt. % "do not provide sufficient foam viscosity enhancement or thickening."

Other cosmetic and cleansing compositions have also included saccharides, but the ability of the saccharides to enhance or boost the foaming characteristics of the compositions have not been defined. Further, the specific compositional makeup of the saccharides in these references lacks specificity. By way of example, U.S. Pat. No. 3,998,761 concerns a hair conditioner that includes beer concentrate. The beer concentrate is said to have a mixture of proteins and polysaccharides. Also, U.S. Pat. No. 3,988,438 discloses a shampoo that has "sugar" present in the shampoo at 0.5 wt. % and a sugar alcohol (sorbitol) present at 10 wt. %. U.S. Pat. No. 5,888,951 discloses a list of various polyols that can be included in a gel-based cleansing composition.

SUMMARY OF THE INVENTION

The present invention overcomes deficiencies in the art by providing a specific blend of saccharides that can be used as a foam enhancer or booster for any given formulation. The blend can include, based on the total weight of the blend, 30 wt. % to 50 wt. % of an aldohexose (e.g., glucose and/or dextrose), 20 wt. % to 55 wt. % of a ketohexose (e.g., fructose), and 10 wt. % to 25 wt. % of a disaccharide (e.g., maltose). The blend can also include 3 wt. % to 10 wt. %, based on the total weight of the blend, of a trisaccharide (e.g., maltotriose), and 5 wt. % to 20 wt. % of higher level saccharides (e.g., at least 4 monosaccharide units, preferably 4 to 20 or more preferably 4 to 10 units). This blend can then be added to any given product formulation to enhance the foaming capabilities of the formulation. Notably, and as illustrated in non-limiting embodiments in the specification, it was discovered that amounts as low as 1 wt. % to 10 wt. % of the blend can be used to enhance the foaming capabilities of any given formulation (formulation and composition can be used interchangeably throughout this specification). Further, it was also discovered that the foam boosting blend of the present invention can be safely added to any given foaming formulation without having to subsequently adjust the proportions of foaming agents (i.e., surfactants and/or detergents) that are already present in the formulation. Without wishing to be bound by theory, it is believed that the foam boosting blend of the present invention is relatively inert when added to a given formulation in that the blend does not appear to negatively affect or chemically react with the existing foaming agents in the formulation. Therefore, the blend can be added to any given formulation without the risk of having to change the foaming agents, the concentration levels of the foaming agents, or add additional ingredients to maintain foamability or stability of the formulation. This is advantageous in that once a foamable product formulation has been formulated, the foam boosting blend of the present invention can be easily added to boost the foaming capabilities of the formulation. Minimal or no further formulating is necessary by the addition of the foam boosting blend of the present invention.

In one aspect of the present invention, there is disclosed a foam booster comprising, consisting essentially of, or consisting of a saccharide blend having a combination of an aldohexose, a ketohexose, and a disaccharide, and optionally a trisaccharide and longer chain polysaccharides. In some instances, the foam boosting blend is in powdered or particulate form prior to being added to a given formulation. In other aspects, the foam boosting blend can be in liquid form, semi-solid form, gelled form, etc. prior to being added to a given formulation. In some preferred embodiments, the foam boosting polysaccharide blend is in liquid form and can be a transparent or opaque liquid. The viscosity of the foam booster can be 1000 cps to 50000 cps, preferably 1000 cps to 10000 cps, or more preferably 4000 cps to 7000 cps, as measured by a Brookfield Viscometer DV-E Model RVDVE spindle #4 at 30 rpm at 25 degrees ° C. The foam booster can include at least 50% solids, preferably 75% to 99% solids. In some more preferred aspects, the foam booster saccharide blend can include 30 wt. % to 50 wt. % of an aldohexose or mixture of aldohexoses, 20 wt. % to 55 wt. or 20 wt. % to 40 wt. % of a ketohexose or mixture of ketohexoses, and 10 wt. % to 25 wt. % of a disaccharide or mixture of disaccharides. In preferred embodiments, the blend can include 35 wt. % to 45 wt. % of an aldohexose or mixture of aldohexoses, 25 wt. % to 30 wt. % of a ketohexose or mixture of ketohexoses, and 12 wt. % to 20 wt. % of a disaccharide or mixture of disaccharides. However, and in additional embodiments, the wt. % ranges can go below our above the stated ranges. For example, the blend can include 5 wt. % to 75 wt. % of an aldohexose or mixture of aldohexoses, 5 wt. % to 75 wt. % of a ketohexose or mixture of ketohexoses, and 5 wt. % to 75 wt. % of a disaccharide or mixture of disaccharides. In more preferred embodiments, the aldohexose is glucose or dextrose, or preferably a combination thereof, the ketohexose is fructose, and the disaccharide is maltose. The blend can also include a trisaccharide (e.g., maltotriose). The amount of the trisaccharide can be 1 wt. % to 20 wt. %, preferably 3 wt. % to 10 wt. % of the blend. In some instances, the blend of the present invention can also include polysaccharides having at least 4 monosaccharide units, preferably 4 to 20 monosaccharide units, and more preferably 4 to 10 monosaccharide units. These longer chain polysaccharides can be the result of unassisted lysis of a larger polysaccharide and may not be specified. The foam boosting saccharide blend of the present invention can increase foaming power as characterized by a foam height increase greater than 10% measured according to a cylinder shake method for an aqueous composition containing distilled water, 0.50 wt. % of a foaming surfactant, and 1 wt. % to 10 wt. % of the foam booster as compared to the aqueous composition without the foam booster.

In another aspect of the present invention there is disclosed a composition that includes the foam boosting saccharide blend of the present invention. The composition is generally a liquid composition (e.g., solution or emulsion). In preferred instances, the composition can include 1 to 20 wt. %, preferably 1 wt. % to 10 wt. %, 1 wt. % to 8 wt. %, 3 wt. % to 8 wt. %, or 3 wt. % to 10 wt. % of the foam booster blend. The composition can further include a foaming agent such as a surfactant or detergent. Non-limiting examples of foaming surfactants and detergents include nonionic, anionic, cationic or amphoteric surfactants, or combinations thereof. Non-limiting examples of nonionic surfactants include polyethoxylated compounds, polypropoxylated compounds, alkanolamides, amine oxides, or fatty acids of polyhydric alcohols, or combinations thereof. Non-limiting examples of anionic surfactants include carboxylates (e.g., alkylcarboxylates and polyalkoxycarboxylates, alcohol ethoxylate carboxylates, or nonylphenol ethoxylate carboxylates or combinations thereof), sulfonates (e.g., alkylsulfonates, alkylbenzenesulfonates, alkylarylsulfonates, or sulfonated fatty acid esters, or combinations thereof), or sulfates (e.g., sulfated alcohols, sulfated alcohol ethoxylates, sulfated alkylphenols, alkylsulfates, sulfosuccinates, or alkylether sulfates, or combinations thereof), or combinations thereof. Non-limiting examples of cationic surfactants include monovalent quaternary ammonium salts, ammonium compounds, amidoamines, or imides, or combinations thereof. Non-limiting amphoteric surfactants include alkylamides, betaines, imidazolines, propionates or sulfobetaines, or combinations thereof. In some aspects, the composition further includes a fragrance, preferably in an amount of 0.5 wt. % to 15 wt. %, preferably 1 wt. % to 15 wt. %, or more preferably 2 wt. % to 15 wt. %. The pH of the composition can range from 1 to 14 depending on the type of composition that the foam boosting blend of the present invention is being added too. In some aspects, the composition is a cosmetic or pharmaceutical composition. The pH of the cosmetic or pharmaceutical composition can be 2 to 10, preferably 3 to 8. In particular embodiments, the composition is a cleansing composition such as a shampoo, body wash, soap, hand cleanser, etc. The pH of the cleansing composition can be preferably 2 to 8, more preferably 4 to 7. In still other aspects, the composition can be an industrial cleansing composition or a fracking or drilling fluid. Non limiting examples of industrial cleansing compositions include rust cleaners, metal cleaners, toilette cleaners, cleansers used to wash cars, laundry, etc. The pH of the industrial cleansing compositions can be 1 to 14 pH, preferably 3 to 10 pH. The pH of the fracking or drilling fluid can be 1 to 14 pH, preferably 8 to 11 pH.

Also disclosed in the context of the present invention is a method of foaming, increasing the foaming capacity, increasing the foam height, increasing the foaming volume, increasing the foam load capacity, increasing the foam load power, or increasing foam stability of a composition. The method can include combining the foam boosting saccharide blend of the present invention with a liquid composition in an amount sufficient to foam, increase foam capacity, increase foam height, increase foam volume, increase foam load capacity, increase foam load power, or increase foam stability of the composition. The foam booster can increase foaming power of the composition as characterized by a foam height increase greater than 10% measured according to a cylinder shake method for the composition having the foam booster as compared to the composition without the foam booster. In preferred aspects, the foam booster of the present invention is added to the composition in an amount of 1 wt. % to 20 wt. %, preferably 1 wt. % to 10 wt. %, 1 wt. % to 8 wt. %, 3 wt. % to 8 wt. %, or 3 wt. % to 10 wt. % of the foam booster blend, based on the total weight of the composition. The composition can be a foamable composition or a non-foamable composition. The composition can be any one of those discussed about and throughout the present specification.

Also disclosed are the following Embodiments 1 to 41 of the present invention. Embodiment 1 is a foam booster comprising a saccharide blend having: (a) 30 wt. % to 50 wt. % of an aldohexose or mixture of aldohexoses; (b) 20 wt. % to 55 wt. % of a ketohexose or mixture of ketohexoses; and (c) 10 wt. % to 25 wt. % of a disaccharide or mixture of disaccharides. Embodiment 2 is the foam booster of Embodiment 1, having: (a) 35 wt. % to 45 wt. % of an aldohexose or mixture of aldohexoses; (b) 25 wt. % to 30 wt. % of a ketohexose or mixture of ketohexoses; and (c) 12 wt. % to 20 wt. % of a disaccharide or mixture of disaccharides. Embodiment 3 is the foam booster of any one of Embodiments 1 to 2, wherein the aldohexose is glucose or dextrose, or a combination thereof, the ketohexose is fructose, and the disaccharide is maltose. Embodiment 4 is the foam booster of any one of Embodiments 1 to 3, further comprising a trisaccharide. Embodiment 5 is the foam booster of Embodiment 4, wherein the trisaccharide is maltotriose. Embodiment 6 is the foam booster of any one of Embodiments 4 to 5, comprising 3 wt. % to 10 wt. % of the trisaccharide. Embodiment 7 is the foam booster of any one of Embodiments 1 to 6, further comprising 5 wt. % to 20 wt. % polysaccharides with at least 4 monosaccharide units, preferably 4 to 20 monosaccharide units, and more preferably 4 to 10 monosaccharide units. Embodiment 8 is the foam booster of any of Embodiments 1 to 7, wherein the foam booster increases foaming power as characterized by a foam height increase greater than 10% measured according to a cylinder shake method for an aqueous composition containing distilled water, 0.50 wt. % of a foaming surfactant, and 1 wt. % to 10 wt. % of the foam booster as compared to the aqueous composition without the foam booster. Embodiment 9 is the foam booster of any one of Embodiments 1 to 8, wherein the foam booster is in powdered and/or particulate form. Embodiment 10 is the foam booster of any one of Embodiments 1 to 8, wherein the foam booster is in liquid form. Embodiment 11 is the foam booster of Embodiment 11, wherein the viscosity of the foam booster is 1000 cps to 50000 cps, preferably 1000 cps to 10000 cps, or more preferably 4000 cps to 7000 cps. Embodiment 12 is the foam booster of any of Embodiments 10 to 11, wherein the liquid is transparent or opaque, preferably transparent. Embodiment 13 is the foam booster of any of Embodiments 1 to 12, wherein the foam booster includes at least 50% solids, preferably 75% to 99% solids. Embodiment 14 is the foam booster of any one of Embodiments 1 to 13, further comprised in a composition. Embodiment 15 is the foam booster of Embodiment 14, wherein the composition comprises 1 wt. % to 20 wt. %, preferably 1 wt. % to 10 wt. %, 1 wt. % to 8 wt. %, 3 wt. % to 8 wt. %, or 3 wt. to 10 wt. % of the foam booster blend. Embodiment 16 is the foam booster of any of Embodiments 14 to 15, wherein the composition further comprises a foaming agent. Embodiment 17 is the foam booster of Embodiment 16, wherein the foaming agent is a surfactant or a combination of surfactants. Embodiment 18 is the foam booster of any of Embodiments 14 to 17, wherein the composition further comprises a fragrance, preferably in an amount of 0.5 wt. % to 15 wt. %, preferably 1 wt. % to 15 wt. %, or more preferably 2 wt. % to 15 wt. %. Embodiment 19 is the foam booster of any of Embodiments 14 to 18, wherein the composition is a cosmetic and/or pharmaceutical composition. Embodiment 20 is the foam booster of Embodiment 19, wherein the composition has a pH of 3 to 8. Embodiment 21 is the foam booster of any one of Embodiments 14 to 19, wherein the composition is a cleansing composition. Embodiment 22 is the foam booster of Embodiment 21, wherein the composition is a shampoo and/or body wash. Embodiment 23 is the foam booster of any one of Embodiments 21 to 22, wherein the composition has a pH of 4 to 7. Embodiment 24 is the foam booster of any one of Embodiments 14 to 18, wherein the composition is an industrial cleansing composition or a fracking and/or drilling fluid. Embodiment 25 is the foam booster of Embodiment 24, wherein the composition is an industrial cleansing composition selected from a rust cleaner, a metal cleaner, and/or a toilette cleaner. Embodiment 26 is the foam booster of Embodiment 24, wherein the composition is a fracking and/or drilling fluid. Embodiment 27 is the foam booster of any one of Embodiments 25 to 26, wherein the composition has a pH of 3 to 11. Embodiment 28 is a method of foaming, increasing the foaming capacity, increasing the foam height, increasing the foaming volume, increasing the foam load capacity, increasing the foam load power, and/or increasing foam stability of a composition, the method comprising combining the foam booster of any one of Embodiments 1 to 13 with a composition in an amount sufficient to foam, increase foam capacity, increase foam height, increase foam volume, increase foam load capacity, increase foam load power, and/or increase foam stability of the composition. Embodiment 29 is the method of Embodiment 23, wherein the foam booster increases foaming power of the composition as characterized by a foam height increase greater than 10% measured according to a cylinder shake method for the composition having the foam booster as compared to the composition without the foam booster. Embodiment 30 is the method of any one of Embodiments 28 to 29, wherein the composition comprises 1 wt. % to 10 wt. % of the foam booster. Embodiment 31 is the method of any one of Embodiments 28 to 30, wherein the composition further comprises a foaming agent. Embodiment 32 is the method of Embodiment 31, wherein the foaming agent is a surfactant or a combination of surfactants. Embodiment 33 is the method of any one of Embodiments 28 to 32, wherein the composition further comprises a fragrance, preferably in an amount of 0.5 wt. % to 15 wt. %, preferably 1 wt. % to 15 wt. %, or more preferably 2 wt. % to 15 wt. %. Embodiment 34 is the method of any one of Embodiments 28 to 33, wherein the composition is a cosmetic and/or pharmaceutical composition. Embodiment 35 is the method of Embodiment 34, having a pH of 3 to 8. Embodiment 36 is the method of any one of Embodiments 28 to 34, wherein the composition is a cleansing composition. Embodiment 37 is the method of Embodiment 36, wherein the composition is a shampoo and/or body wash. Embodiment 38 is the method of any one of Embodiments 36 to 37, wherein the composition has a pH of 4 to 7. Embodiment 39 is the method of any one of Embodiments 28 to 33, wherein the composition is an industrial cleansing composition or a fracking and/or drilling fluid. Embodiment 40 is the method of Embodiment 39, wherein the composition is an industrial cleansing composition selected from a rust cleaner, a metal cleaner, and/or a toilette cleaner. Embodiment 41 is the method of Embodiment 40, wherein the composition is a fracking and/or drilling fluid.

"Foam" refers to liquid foams or foams obtain from a liquid composition. A foam is a mass of bubbles that are formed in or on a liquid. The foam is formed by trapping pockets of gas in the liquid such that thin films of the liquid separate the pockets of gas. The foam can be created, for example, by mechanically agitating the liquid (e.g., applying a physical force to the liquid so as to generate shearing strain on and deform the foamable liquid—e.g., rubbing/lathering the liquid with hands such as washing a person's hands or hair or skin) or introducing gas into the liquid (e.g. a dispenser that is liquid inside the container but is expelled as a foam when existing the container due to the introduction of a gas such as air or gas propellants into the liquid). Foam in the context of the present invention does not refer to solid foams (e.g., a polyurethane foam, a carbon foam, a ceramic foam, etc.).

The "foam booster" or "foam enhancer" of the present invention includes the saccharides disclosed throughout this specification that have been combined together to create a blend. The blend can then be added to any given liquid formulation that includes a foaming agent. The blend can increase the surface viscosity of the liquid which surrounds/constitutes/makes-up the bubbles in the foam, thereby increasing the foam load capacity, foam height, and/or foam stability.

"Foaming agent" is any compound that enable a composition to form a foam. Non-limiting examples of foaming agents include detergents, foaming surfactants, and other compounds associated with generating foam.

"Foam load capacity" refers to the amount of a substance that a foam can carry while still maintaining a foam structure. The foam load capacity may be defined in relation to the substance in or on the foam structure, such as by the weight or mass of the substance in or on the foam, or load capacity may be defined in relation to the substance in a foamable composition, such as by the weight, mass, or concentration of a substance in a liquid composition that is to be foamed or has been foamed. When the foam load capacity for a substance has been exceeded, the foam loses its foam structure.

"Foam height" and "foam volume each refer to the height or volume of the foam above any non-foamed portion of a foamable composition.

"Foam power" and "foaming power" each refer to a foam height increase greater than 10% as measured according to a cylinder shake method for an aqueous composition containing distilled water, 0.50 wt. % of a foaming surfactant, and 1 wt. % to 10 wt. % of the foam booster of the present invention as compared to the aqueous composition without the foam booster.

"Foam stability" refers to the time required for the foam to collapse or no longer create foam despite a form of agitation or introduction of gas. The longer the time it takes the foam to collapse generally equates to increased foam stability.

"Anti-foaming agent" refers to a compound that decreases a characteristic associated with a foam when the compound is added or the concentration of the compound is increased in a foamable composition. Non-limiting examples of characteristics associated with a foam include foam load capacity, foam height, foam volume, and foam stability. Non-limiting examples of anti-foaming agents include oils, fragrances, and solids.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The foam boosting blend, compositions having the foam boosting blend, and methods of using the foam boosting blend of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the foam boosting blend of the present invention is its ability to increase foam load capacity, foam height, foam volume, foam power, and/or foam stability of a given foamable composition.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain non-limiting aspects of the present invention. The invention may be better understood by reference to one or more of these drawings in combination with the detailed description of specific embodiments presented herein.

Figure 1A:
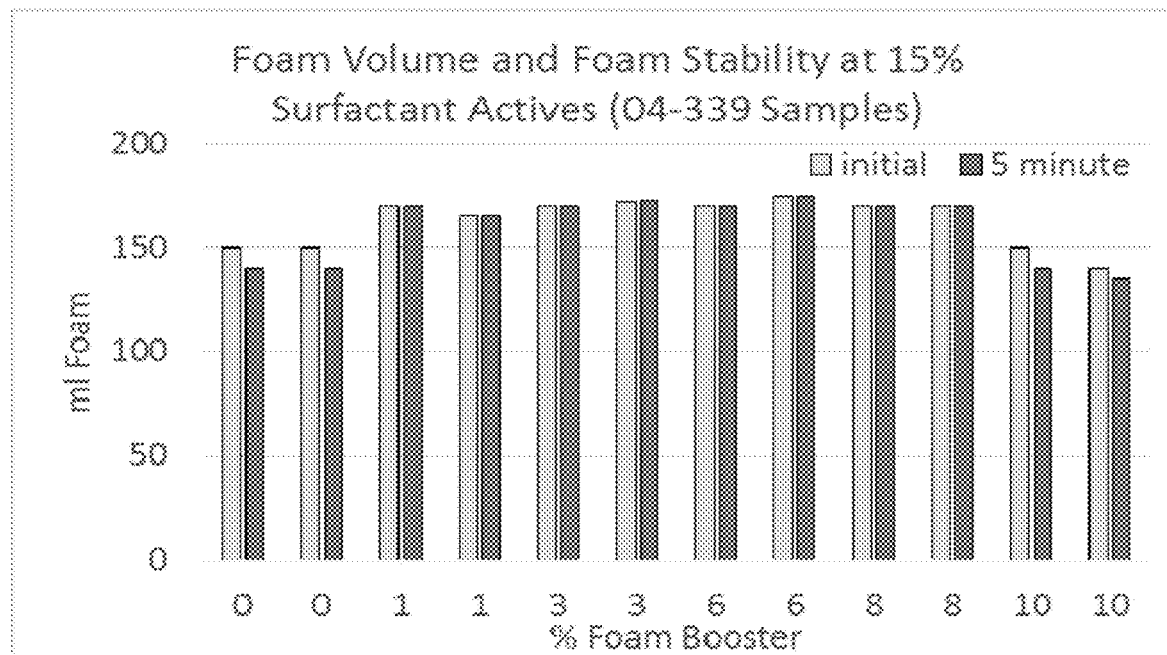
FIGS. 1A and 1B—Show foam volume and foam stability at 15% surfactant actives for several formulations containing foam boosting blend at different concentrations. The foam boosting blend provides an increase in foam volume and foam stability.
Figure 1B:
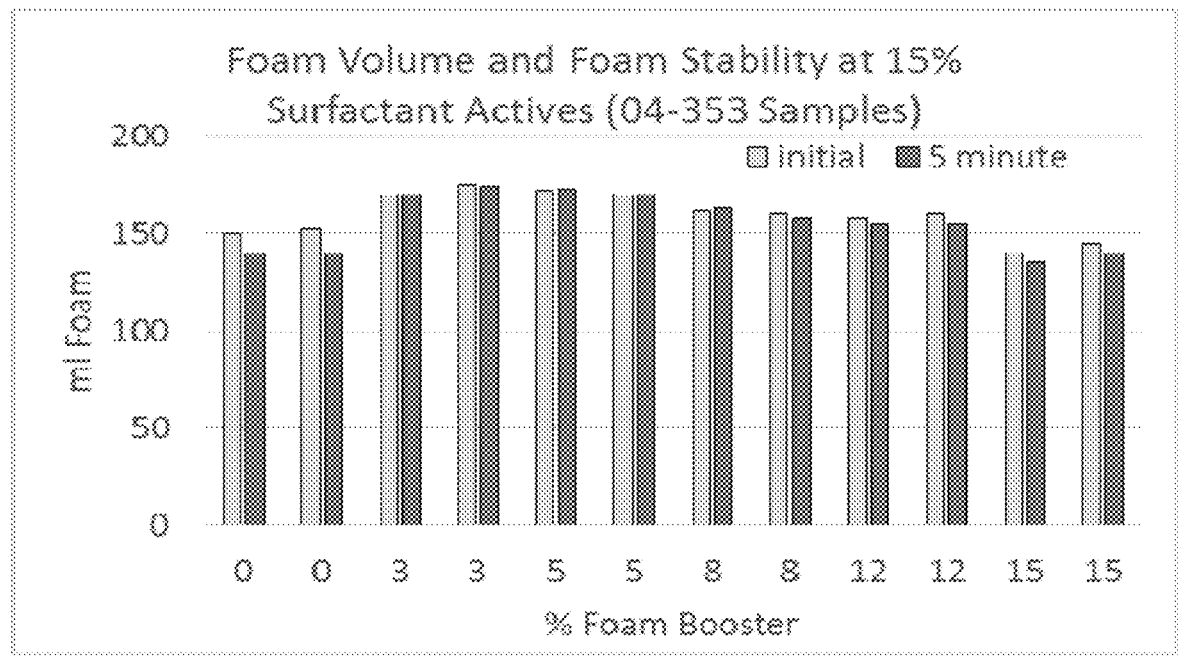
Figure 2A:
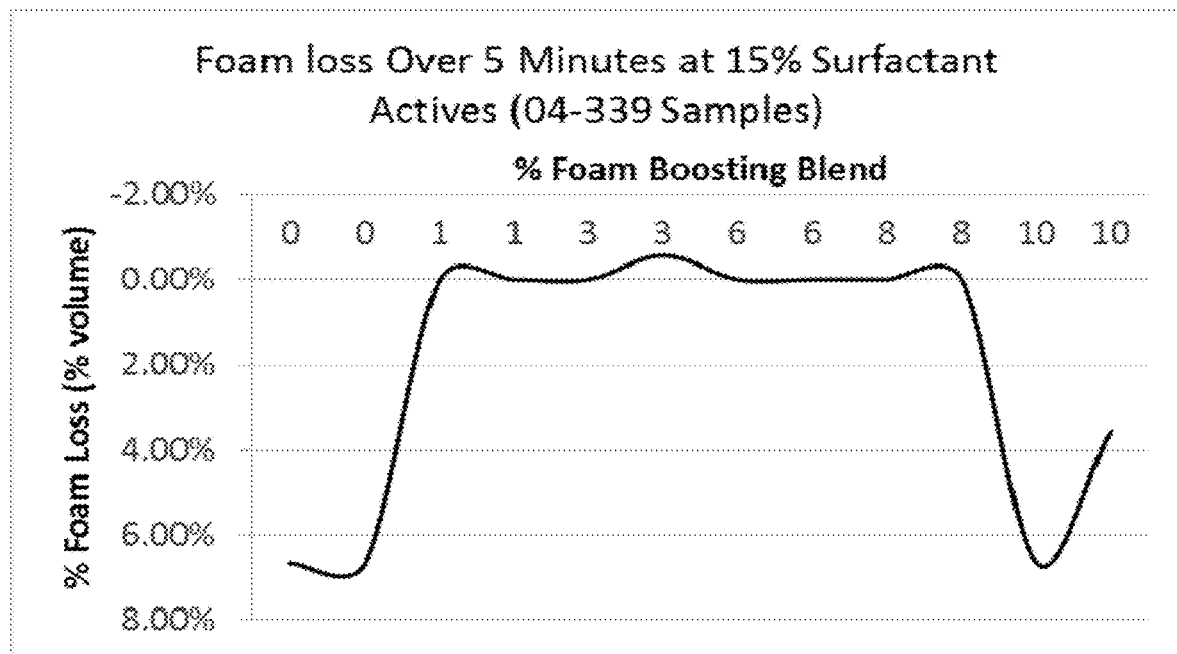
FIGS. 2A and 2B—Show foam loss over 5 minutes at 15% surfactant actives for several formulations containing foam boosting blend at different concentrations. The foam boosting blend provides a decrease in foam loss.
Figure 2B:
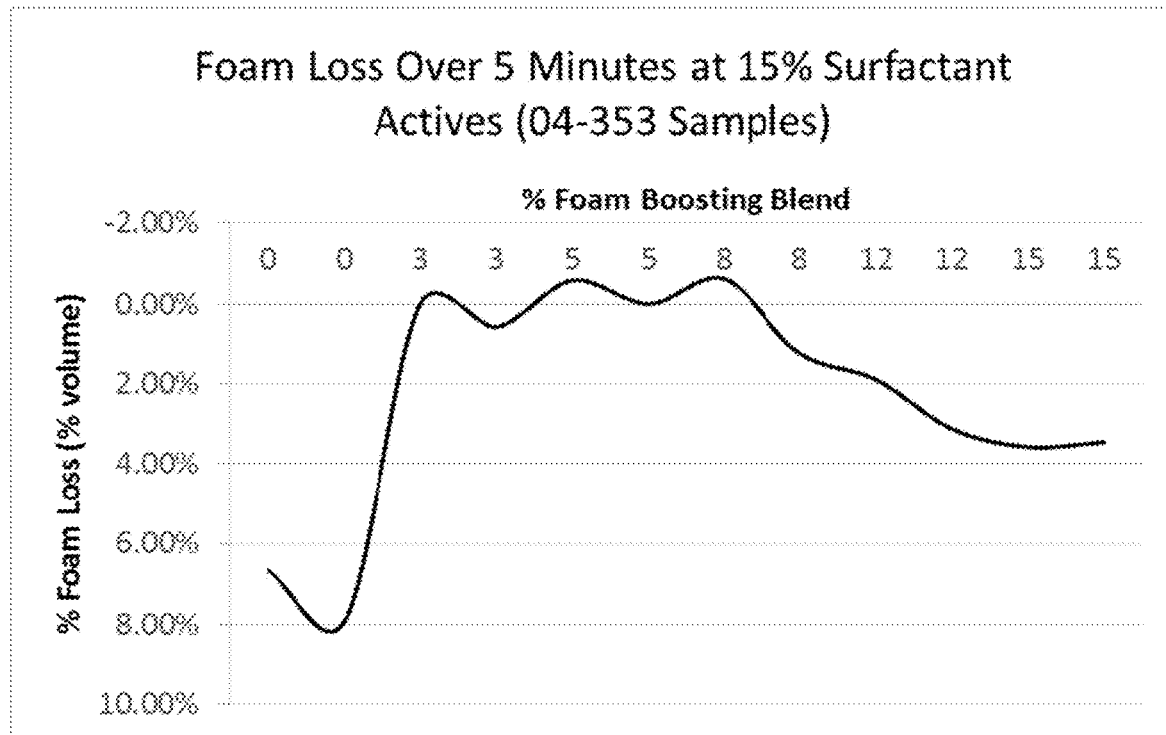

While the invention is susceptible to various modifications and alternative forms, specific embodiments thereof are shown by way of example in the drawings and may herein be described in detail.

DESCRIPTION OF ILLUSTRATIVE EMBODIMENTS

Currently available foam boosters such as alkylaminocarboxylic acid salts, fatty acid amides, fatty acid alkanolamides, betaines, sulfobetaines, polymeric compounds, or mixtures thereof, can be expensive to use, can cause skin irritation, and can be chemically reactive and prone to react with other ingredients in a given product formulation, thereby introducing instability into the formulation. Further, while some attempts have been made at using saccharides as foam boosters, the amount needed to be incorporated into a given formulation can be prohibitively high and can negatively affect the tactile properties and stability of a given formulation.

The foam boosting saccharide blend of the present invention offers a solution to these issues. The solution is premised on a specific combination or blend of saccharides that results in an effective foam booster. The blend can include a combination of aldohexoses, ketohexoses, disaccharides, and optionally trisaccharides and longer chain saccharides (e.g., 4 or more monosaccharide units, preferably 4 to 20 monosaccharide units, or more preferably 4 to 10 monosaccharide units). This saccharide blend can be less caustic to skin and can be less reactive to ingredients such as foaming agents that are present in a given foamable liquid formulation. Therefore, the addition of the saccharide blend to any given formulation can be used to enhance the foaming properties of the formulation without requiring the formulator to make substantial revisions to the product formulation.

These and other non-limiting aspects of the present invention are discussed in further detail in the following sections.

A. Foam Boosting Saccharide Blend

1. Saccharide Components

An aldohexose is typically a hexose containing an aldehyde. Examples of aldohexoses that can be include in the foam booster include, but are not limited to, allose, altrose, glucose, mannose, gulose, idose, galactose, and talose. Preferably, the aldohexose is glucose, dextrose, or a combination thereof. Aldohexoses such as glucose and dextrose are commercially available from a wide range of suppliers (e.g., Sigma-Aldrich Co. LLC (St. Louis, Mo., USA); Parchem fine & specialty chemicals, New Rochelle, N.Y., USA; Honeywell Specialty Chemicals (Morristown, N.J. USA); Corn Products International (Westchester, Ill. USA); Nippon Starch Chemical (Osaka Japan)). The amount of aldohexose in the foam boosting saccharide blend can be 30 wt. % to 50 wt. % based on the total weight of the blend. However, ranges below 30 wt. % and above 50 wt. % are also contemplated in the context of the present invention (e.g., 1 wt. % to 99 wt. %, or 5 wt. % to 75 wt. %).

A ketohexose is typically a hexose containing a ketone. Examples of ketohexoses that can be include in the foam booster include, but are not limited to, fructose, psicose, sorbose, and tagatose. Preferably, the ketohexose is fructose. Ketohexoses such as fructose are commercially available from a wide range of suppliers (e.g., Sigma-Aldrich Co. LLC (St. Louis, Mo., USA); Parchem fine & specialty chemicals, New Rochelle, N.Y., USA; Honeywell Specialty Chemicals (Morristown, N.J. USA); Corn Products International (Westchester, Ill. USA); Nippon Starch Chemical (Osaka Japan)). The amount of ketohexose in the foam boosting saccharide blend can be 20 wt. % to 55 wt. %, or 20 wt. % to 40 wt. %, based on the total weight of the blend. However, ranges below 20 wt. % and above 55 wt. % are also contemplated in the context of the present invention (e.g., 1 wt. % to 99 wt. %, or 5 wt. % to 75 wt. %).

A disaccharide is a compound made of two monosaccharides covalently bound together. A disaccharide is also known as a biose or a double sugar. Examples of disaccharides that can be include in the foam booster include, but are not limited to, lactose, maltose, and sucrose. Preferably, the disaccharide is maltose. Disaccharides such as maltose are commercially available from a wide range of suppliers (e.g., Sigma-Aldrich Co. LLC (St. Louis, Mo., USA); Parchem fine & specialty chemicals, New Rochelle, N.Y., USA; Honeywell Specialty Chemicals (Morristown, N.J. USA); Corn Products International (Westchester, Ill. USA); Nippon Starch Chemical (Osaka Japan)). The amount of disaccharide in the foam boosting saccharide blend can be 10 wt. % to 25 wt. % based on the total weight of the blend. However, ranges below 10 wt. % and above 25 wt. % are also contemplated in the context of the present invention (e.g., 1 wt. % to 99 wt. %, or 5 wt. % to 75 wt. %).

A trisaccharide is a compound made of three monosaccharides covalently bound together. Examples of trisaccharides that can be include in the foam booster include, but are not limited to, isomaltotriose, kestose, maltotriose, maltotriulose, melezitose, and raffinose. Preferably, the trisaccharide is maltotriose. Trisaccharides such as maltotriose are commercially available from a wide range of suppliers (e.g., Sigma-Aldrich Co. LLC (St. Louis, Mo., USA); Parchem fine & specialty chemicals, New Rochelle, N.Y., USA; Honeywell Specialty Chemicals (Morristown, N.J. USA); Corn Products International (Westchester, Ill. USA); Nippon Starch Chemical (Osaka Japan)). The amount of trisaccharide in the foam boosting saccharide blend can be 3 wt. % to 10 wt. % based on the total weight of the blend. However, ranges below 3 wt. % and above 10 wt. % are also contemplated in the context of the present invention (e.g., 1 wt. % to 99 wt. %, or 1 wt. % to 75 wt. %).

A polysaccharides with at least 4 monosaccharide units can be a linear or branched polymer. Examples of polysaccharides that can be include in the foam booster include, but are not limited to, amylopectin, amylose, arabinoxylan, callose, cellulose, chitin, chysolaminarin, fucoidan, galactomannan, glycogen, laminarin, and mannan. Preferably, the polysaccharide is made up of 4 to 30 monosaccharide units, preferably 4 to 20 monosaccharide units, and more preferably 4 to 10 monosaccharide units. A polysaccharide may be the lysis product of a larger polysaccharide. Preferably, the polysaccharide is a lysis product of a starch. More preferably, the polysaccharide is a lysis product of cornstarch. Even more preferably, the polysaccharide is a hydrolysis product of cornstarch. In some instances, the polysaccharides included in the foaming boosters disclosed herein occur through unassisted lysis of a larger polysaccharide and may not be specified. Polysaccharides are commercially available from a wide range of suppliers (e.g., Sigma-Aldrich Co. LLC (St. Louis, Mo., USA); Parchem fine & specialty chemicals, New Rochelle, N.Y., USA; Honeywell Specialty Chemicals (Morristown, N.J. USA); Corn Products International (Westchester, Ill. USA); Nippon Starch Chemical (Osaka Japan)). The amount of polysaccharide having at least 4 monosaccharide units in the foam boosting saccharide blend can be 5 wt. % to 20 wt. % based on the total weight of the blend. However, ranges below 5 wt. % and above 20 wt. % are also contemplated in the context of the present invention (e.g., 1 wt. % to 99 wt. %, or 1 wt. % to 75 wt. %).

2. Non-Saccharide Components and Characteristics of the Foam Boosting Polysaccharide Blend The foam boosting polysaccharide blend of the present invention can include other ingredients. For example, additional ingredients can be added to modify the rheological properties of the foam boosters or the pH of the foam boosters. In a preferred embodiment, a foam booster contains 75% to 99% solids. In another preferred embodiment, a foam booster contains a minimum of 80% solids, 80% to 88%, 80% to 86%, 82% to 88%, 82% to 86%, 80% to 90%, 82% to 90%, 75% to 88%, or 75% to 86% solids. In a preferred embodiment, a foam booster has a viscosity of 1000 to 50000 cps, as measure by a Brookfield Viscometer DV-E Model RVDVE spindle #4 at 30 rpm at 25 degrees ° C. In more preferred embodiments, the viscosity if the blend can be 1000 to 10000 cps, 3000 to 7000 cps, or about 4000 to 6000 cps or even more preferably about 4000 to 5300 cps, 4200 to 5700 cps, 4200 to 5300 cps, 4200 to 6000 cps, or 4000 to 5700 cps. In a preferred embodiment, a foam booster has a pH of 1 to 14 or any range therein. In another preferred embodiment a foam booster has a pH of 2 to 12, 3 to 12, 3 to 8, 3 to 7, 4 to 12, 4 to 8, or 4 to 7. In a preferred embodiment the foam booster is in liquid form. The liquid can be transparent or opaque.

3. Method of Making the Foam Boosting Saccharide Blend

The foam boosting saccharide blend of the present invention can be made by obtaining each of the components of the blend (i.e., aldohexose, ketohexose, disaccharide, and optionally trisaccharides and polysaccharides having 4 or more monosaccharide units) and mixing the components together to for a mixture. In some instances, each of the components are in powdered or particulate form, such that the resulting mixture or blend is in powdered or particulate form. In other instances, each of the components are in liquid form and the resulting mixture or blend is in liquid or an otherwise flowable form. In preferred aspects of the present invention, the blend is a mixture of the individual components dissolved in an aqueous solution. Without wishing to be bound by theory, it is believed that each component is chemically inert to the other components in the blend. The following includes a non-limiting process that can be used to make a foam boosting saccharide blend of the present invention:

a. In a suitable clean and sterile vessel add the components of the blend under mixing conditions (e.g., suitable marine or A310 blade of appropriate dimension scaled to the vessel attached to a mixer capable of 300-1000 rpm). Do not overmix to prevent the introduction of excessive air bubbles into the batch.

b. Continue mixing until a uniform solution is formed. In preferred embodiments, the uniform solution can be transparent.

c. Increase speed as needed to maintain turnover without introducing excessive shear.

d. Once completed discontinue mixing.

The mixing process can be performed without heating the components or mixture. Therefore, the temperature of the blend during manufacture (e.g., during the above mixing steps) can be substantially the same as room temperature (e.g., 15° C. to 30° C., preferably 20° C. to 25° C., or about 25° C.).

4. Effects of the Foam Boosting Saccharide Blend on a Composition

The foam boosting saccharide blend of the present invention can modify the foam characteristics of a given composition (e.g., either a liquid composition or a non-liquid composition that, when added with water, can produce foam such as a solid bar of hand soap). As non-limiting examples, a foam boosting saccharide blend of the present invention can make a non-foamable composition foamable. In other instances, the blend can increase foaming power, increase foam quantity, increase foam stability, increase foam density, increase the foam's load capacity, modify the foam texture, and/or increase the speed at which a foam is created of a given composition.

Methods of measuring the characteristics of a foam and of a foam booster are known in the art. For example, foaming power and foam stability can be characterized by measuring the foam height or volume of a composition according to a cylinder shake method. The cylinder shake method can be performed by preparing a test composition of liquid that contains a foaming agent and with/without a foam booster, placing the test composition in a cylinder and stoppering the cylinder, agitating the test composition by vigorously shaking the cylinder vertically for a set period of time, and immediately measure the volume or height of the foam in the cylinder at the completion of the agitation step. Increased foam volume or height indicates increased foam power. Foam stability can be characterized by then determining the rate of decrease in volume or height of the foam over time while the test composition is undisturbed. Increased foam stability is indicated by a slower reduction in foam volume or height. In one embodiment, foaming power and foam stability are determined using distilled water as the liquid, 0.50 wt. % of a foaming surfactant, and with/without 1 wt. % to 10 wt. % foam booster.

B. Methods of Using the Foam Boosting Saccharide Blend

The foam boosting saccharide blend of the present invention can be used to modify the foam characteristics of a composition. As non-limiting examples, the foam boosters can enable a non-foamable composition to become foamable, increase foaming power, increase foam quantity, increase foam stability, increase foam density, increase the foam's load capacity, modify the foam texture, and/or increase the speed at which a foam is created. As further non-limiting examples, the foam boosters can increase the number of suitable foaming agents capable of creating desired foam characteristics in a composition, decrease the concentration of foaming agents needed to form a foam with desired characteristics, and/or prevent modification of foam characteristics by increasing the concentration of an agent that modifies foam characteristics, such as anti-foaming agents.

The foam boosting saccharide blend of the present invention can be used in a large variety of compositions. Non-limiting examples of such compositions include pharmaceutical compositions, cosmetics, personal care products, food stuffs, cleansing compositions, extraction compositions, fracking fluid, drilling fluid, and gas capture compositions. Preferably, the foam boosters are non-toxic and non-irritants. In some preferred embodiments, the foam boosters may be used in, but are not limited to, pharmaceuticals and/or cosmetics.

The foam booster can be combined in a composition at any concentration. Preferably, the foam booster concentration is sufficient to increase, modify, or maintain a foam characteristic of the composition. Non-limiting concentrations of the foam booster include at least about 0.0001 wt. % to 99 wt. % of the composition, or any range derivable therein. In a preferred embodiment, a composition contains 1 wt. % to 20 wt. %, 1 wt. % to 15 wt. %, 1 wt. % to 10 wt. %, 3 wt. % to 15 wt. %, 3 wt. % to 10 wt. %, 1 wt. % to 8 wt. %, or 3 wt. % to 8 wt. % of the foam booster blend of foam booster.

The foam booster can be combined in a composition that contains other ingredients including, but not limited to, active ingredients, foaming agents, anti-foaming agents, vehicles, carriers, structuring agents, cosmetic ingredients, pharmaceuticals, cleaning agents, fragrances, buffers, solids, oils, etc. The vehicle or carrier can be a pharmaceutically or dermatologically acceptable vehicle or carrier. Non-limiting examples of vehicles or carriers include water, glycerin, alcohol, oil, a silicon containing compound, and a silicone compound. In a preferred embodiments the composition contains one or more foaming agent, such as one or more surfactants. The foaming agent can be a pharmaceutically or dermatologically acceptable surfactant or detergent. Non-limiting examples of foaming surfactants and detergents include nonionic, anionic, cationic or amphoteric surfactants, or combinations thereof. Non-limiting examples of nonionic surfactants include polyethoxylated compounds, polypropoxylated compounds, alkanolamides, amine oxides, or fatty acids of polyhydric alcohols, or combinations thereof. Non-limiting examples of anionic surfactants include carboxylates (e.g., alkylcarboxylates and polyalkoxycarboxylates, alcohol ethoxylate carboxylates, or nonylphenol ethoxylate carboxylates or combinations thereof), sulfonates (e.g., alkylsulfonates, alkylbenzenesulfonates, alkylarylsulfonates, or sulfonated fatty acid esters, or combinations thereof), or sulfates (e.g., sulfated alcohols, sulfated alcohol ethoxylates, sulfated alkylphenols, alkylsulfates, sulfosuccinates, or alkylether sulfates, or combinations thereof), or combinations thereof. Non-limiting examples of cationic surfactants include monovalent quaternary ammonium salts, ammonium compounds, amidoamines, or imides, or combinations thereof. Non-limiting amphoteric surfactants include alkylamides, betaines, imidazolines, propionates or sulfobetaines, or combinations thereof. The composition can contain one or more anti-foaming agents. Non-limiting examples anti-foaming agent include oils (e.g., sunflower oil, coconut oil, vegetable oils, plant oils, skin moisturizers, etc.), fragrances, or solids.

The foam boosters can be combined in compositions structured or formulated in a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), solutions (both aqueous, hydro-alcoholic, and others), anhydrous bases, and gels. Variations of a composition containing a foam booster described herein will be apparent to the skilled artisan and are appropriate for use in the present invention.

All of the foam boosters, compositions, and methods disclosed and claimed herein can be made and executed without undue experimentation in light of the present disclosure. While the compositions and methods of this invention have been described in terms of preferred embodiments, it will be apparent to those of skill in the art that variations may be applied to the foam boosters, compositions, and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Method of Making a Foam Boosting Saccharide Blend

A foam boosting blend was prepared by combining at a 1:1 ratio FARMAL® HFS 2656 and FARMAL® GS 1653. FARMAL® HFS 2656 and FARMAL® GS 1653 are both commercially available from Ingredion and are aqueous solutions of carbohydrates produced through the hydrolysis of corn starch. FARMAL® HFS 2656 and FARMAL® GS 1653 have the characteristics disclosed in Table 1.

TABLE 1

|  | Appearance | Density (kg/liter) v. Temperature | Viscosity (cps) v. Temperature | Dry Substance % | pH (as is) |
|---|---|---|---|---|---|
| FARMAL® HFS 2656 | clear, slightly viscous liquid | 1.379 at 80° F. <br> 1.372 at 100° F. <br> 1.367 at 120° F. | 700 at 80° F. <br> 250 at 100° F. <br> 100 at 120° F. | 76.8 to 77.4 | 3.5 to 4.3 |

| Carbohydrate Profile, % d.b. | |
|---|---|
| Fructose | 55 |
| Dextrose + Fructose | >95.0 |
| Higher Saccharides (with at least 2 monosaccharide units) | <5.0 |

|  | Appearance | Density (kg/liter) v. Temperature | Viscosity (cps) v. Temperature | Dry Substance % | Dextrose Equivalent |
|---|---|---|---|---|---|
| FARMAL® GS 1653 | clear, viscous liquid | 1.421 at 80° F. <br> 1.415 at 100° F. <br> 1.409 at 120° F. | 20000 at 80° F. <br> 5800 at 100° F. <br> 1800 at 120° F. | 81.0 to 82.7 | 60.0 to 67.0 |

| Carbohydrate Profile, % d.b. | |
|---|---|
| Dextrose | 35 |
| Maltose | 30 |
| Maltotriose | 13 |
| Higher Saccharides (with at least 4 monosaccharide units) | 22 |

FARMAL® HFS 2656 and FARMAL® GS 1653 were combined at a 50:50 ratio to form a foam booster under the following process conditions:
  a. In a suitable clean and sterile vessel, preferably anodized with 316 grade stainless steel lined with Chromium or Nickel, FARMAL® HFS 2656 was added to the vessel.
  b. Mixing occurred with a IKA Eurostar 60, Model Euro-ST-60-D-S001 using a A310 blade of at 500-600 rpm.
  c. Visually monitored the mixture to avoid over-mixing. Over-mixing can introduce excessive air into the batch can increase the potential for foam during mixing.
  d. When suitably turned over and uniform, FARMAL® GS 1653 was added to the main vessel with FARMAL® HFS 2656. No external heat source was used in the mixing process.
  e. Blended the two components together until a transparent uniform solution was formed. Increased speed as needed to maintain turnover without introducing excessive shear.
  f. Once completed discontinued mixing and sent the sample for QC.

Multiple batches of the foam booster were prepared as described above and tested for visual appearance, dry substance %, viscosity, and pH. The results follow in Table 2.

TABLE 2

| Batch | Appearance | Viscosity (cps) | Dry Substance % | pH at 25° F. |
|---|---|---|---|---|
| A | clear liquid | 4918 at 25° F. | 85.7 | |
| B | clear liquid | 5200 at 25° F. | 83.4 | |
| C | clear liquid | 5040 at 25° F. | 85.0 | |
| D | clear liquid | 4287 at 25° F. <br> 5260 at 25° F. <br> 5207 at 25° F. | 85.7 | 6.04 at 25° F. <br> 4.44 at 25° F. <br> 4.38 at 25° F. | pH measurements were performed on a 3 point standardized Sartorius pH meter at ambient temperature on the batch after manufacture as part of internal quality control. Viscosity using 600 ml of bulk was performed using a Brookfield viscometer spindle #4 at 30 rpm at 25° C. % solids will be determined using a moisture analyzer.

Example 2

Testing the Foam Boosting Blend

The foam boosting blend (Batch C from Table 2) was added into the foamable formulations described in Tables 3 and 4 by adding the foam boosting blend into the formula via mixing and adjusting the level of aqueous sodium hydroxide used to account for pH drift caused by the boosting blend (i.e., q.s down with aqueous sodium hydroxide). These formulations were tested to determine foam power and foam stability of these formulations with (3 wt. %) and without (0 wt. %) the foam booster.

TABLE 3

| Ingredient | % Concentration (by weight) |
|---|---|
| Phase A | |
| Water | 44 |
| Synthalen® W600 (Acrylates Copolymer) | 10 |
| COAB (Chembetaine™ C Surfactant (Cocamidopropyl Betaine)) | 30 |
| LG-1250 (Endinol® MILD CC-1250 (Coco-Glucoside)) | 10 |
| NaOH 25% w/w (Sodium Hydroxide) | q.s. |
| Phase B | |
| Olivatis™ 15 (Olive Oil Glycereth-8 Esters) | 2 |
| Fragrance Oil (Ultrapure Lavender Oil (*Lavandula Angustifolia* (Lavender) Oil) and Peppermint Essential Oil (*Mentha Piperita* (Peppermint) Oil)) | 3 |

TABLE 3-continued

| Ingredient | % Concentration (by weight) |
|---|---|
| Phase C | |
| Preservative(Sharomix ™ CPP (Caprylyl Glycol (and) Phenylpropanol)) | 1 |
| Foam Booster | 0 or 3 |

TABLE 4

| Ingredient | % Concentration (by weight) |
|---|---|
| Phase A | |
| Water | 38 |
| Synthalen ® W600 (Acrylates Copolymer) | 10 |
| COAB (Chembetaine ™ C Surfactant (Cocamidopropyl Betaine)) | 30 |
| LG-1250 | 10 |
| NaOH 25% w/w (Sodium Hydroxide) | q.s. |
| Phase B | |
| Olivatis ™ 15 (Olive Oil Glycereth-8 Esters) | 2 |
| Fragrance Oil (Ultrapure Lavender Oil (*Lavandula Angustifolia* (Lavender) Oil) and Peppermint Essential Oil (*Mentha Piperita* (Peppermint) Oil))[1] | 9 |
| Phase C | |
| Preservative (Sharomix ™ CPP (Caprylyl Glycol (and) Phenylpropanol)) | 1 |
| Foam Booster | 0 or 3 |

[1]Fragrance oil was a 1:1 blend of lavender oil and peppermint essential oil. Lavender oil was supplied by Ultrapure Laboratories (Ireland). Peppermint essential oil was supplied by D&D Essential Oils (Garland, Texas, USA).

The foam power and stability of formulations with and without the foam booster (Batch C from Table 2) were tested to determine if foam power and stability were increased in formulations that contained foam booster. Formulations as described in Tables 3 and 4 were prepared with (3% by wt.) and without (0% by wt.) the foam booster. The formulations varied in the amount of fragrance oil and water contained therein. Negative controls without foam booster were prepared as described in Tables 3 and 4, with 3 wt. % fragrance oil and no foam booster and with 9 wt. % fragrance oil and no foam booster, respectively. A foam booster containing test formulation was prepared as described in Table 4, with 9 wt. % fragrance oil and 3 wt. % foam booster.

Foam power was tested by the cylinder shake method. Briefly, equal amounts of the negative controls and test formulation were added into individual identical cylinders. Each cylinder was sealed and the formulations were agitated by vigorously shaking the sealed cylinders vertically for 10 seconds. Immediately following agitation, the foam height in each cylinder was measured. Foam power was reported as the foam height immediately after agitation.

Foam stability was determined by measuring the foam height of each formulation after agitation once a minute for 10 minutes. The formulations were left undisturbed during the entire 10 minute measurement period. Foam stability was reported as the rate of decrease in foam height over time. The slower the rate of decrease, the greater the foam stability.

It was found that the 9 wt. % fragrance oil negative control had decreased foam power when compared to the 3 wt. % fragrance oil negative control. It was surprisingly found that the foam booster test formulation with 9 wt. % fragrance oil and 3 wt. % foam booster had increased foam power and stability when compared to the 9 wt. % fragrance oil negative control.

Thus, it was determined that adding a foam booster as disclosed herein will increase the foam power and foam stability of a formulation without having to adjust the proportion of foaming agents in the formulation. Further, it was determined that adding a foam boosting blend as described herein will increase the foam power and stability of formulations with high concentrations of anti-foaming agents, such as formulations with 9 wt. % fragrance oil. It is contemplated that adding a foam booster as described herein to a formulation also mitigates the need to adjust the proportion of foaming agents or anti-foaming agents to avoid noticeable changes in a desired foam characteristic when changes are made to the formulation. As non-limiting examples, the foam boosters as described herein allow one to avoid having to change surfactant type or class, allows one to formulate foamable formulations with high loads of anti-foaming agents or foam modifiers, and/or allows one to avoid adding additional compounds which could interfere with the characteristics of a foam. As further non-limiting examples, the foam boosters as described herein allow one to formulate foamable formulations with pHs and at temperatures that would otherwise prevent formation of a foam.

Example 3

Stability Testing of a Shampoo Having the Foam Boosting Blend

Foam boosting blend from Batch C, Table 2, were added to shampoo formulations based on the ingredient list described in Table 5 below by adding the foam boosting blend into the formula via mixing and adjusting the water to account for the boosting blend (i.e., q.s down with water). The addition of the foam boosting blend provided an observable increase in flash foam, followed by a loose to medium density foam upon contact with water characterized at that point as a stable foam with a longer retention time than expected.

TABLE 5*

| Ingredient | % Concentration (by weight) |
|---|---|
| Phase A | |
| Water | 36 |
| Dissolvin ® GL-47-S (Tetrasodium Glutamate Diacetate) | 0.2 |
| Synthalen ® W600 (Acrylates Copolymer) | 10 |
| Phase B | |
| Chembetaine ™ C Surfactant (Cocamidopropyl Betaine) | 25 |
| Endinol ® MILD CC-1250 (Coco-Glucoside) | 10 |
| Safflower Oil (*Carthamus tinctorius* (Safflower) Seed Oil) | 3 |
| Phase C | |
| Olivatis ™ 15 (Olive Oil Glycereth-8 Esters) | 2 |
| Ultrapure Lavender Oil (*Lavandula Angustifolia* (Lavender) Oil) | 6 |
| Peppermint Essential Oil (*Mentha Piperita* (Peppermint) Oil) | 4 |
| Phase D | |
| NaOH 25% w/w (Sodium Hydroxide) | q.s. |

TABLE 5*-continued

| Ingredient | % Concentration (by weight) |
|---|---|
| Phase E | |
| Sharomix ™ CPP (Caprylyl Glycol (and) Phenylpropanol) | 1 |
| Foam Booster | 3 |
| Excipients** | q.s. |

*Formulation can be prepared by adding Phase A to main vessel with shear mixing. Add Phase B to the main vessel under continued shear mixing. Add Phase C in order to the main vessel under shear mixing. QA Phase D to desired pH. Add Phase E in order under shear mixing. Transfer to final container once uniform.

**Excipients can be added, for example, to modify the rheological properties of the formulation. Alternatively, the amount of water can be varied.

Example 4

Foam Volume, Foam Loss, and Foam Stability Testing of a Soap Having the Foam Boosting Blend Foam boosting blend was added to foaming formulation B-PRV containing 15% surfactant actives based on the ingredient list described in Table 6 by adding the foam boosting blend into the formula via mixing and adjusting the water to account for the boosting blend (i.e., q.s down with water) (see Table 7). The addition of the foam boosting blend at multiple concentration provided an increase in foam volume, increase in foam stability, and a decrease in foam loss (See Table 7 and FIGS. 1A, 1B, 2A, and 2B).

Briefly, for testing, a 0.20% solution of the formulations in Table 7 were made by diluting 0.16 g of the formulations into 79.84 g of water. The dilutions were warmed to 25° C. if needed and 50 ml of the dilution was placed in a 250 ml graduated cylinder and inverted.

TABLE 6*

| Ingredients in B-PRV | % Concentration (by weight) |
|---|---|
| Deionized Water | 64.95% |
| Sodium Lauryl Sulfate (Endinol SLS-N) | 18.00% |
| Sodium Laureth Ether Sulfate 2 mol 70% (Endinol ES-270) | 13.00% |
| Ethylene Glycol Distearate (EGDS) | 3.00% |
| Sodium Chloride | 1.00% |
| Methylchloroisothiazolinone/methylisothiazolinone (MCI/MIT) Sharomix MCI II | 0.05% |
| Excipients** | q.s. |

*The concentration of solids in this formulation is 31.5% by weight
**Citric acid can be added as needed to adjust the pH of the formulation to 6.5 to 7.5 (0.8 g of citric acid was added to this batch). NaCl can be added to thicken and additional water can be added to thin. No additional NaCl or water was added to this batch.

TABLE 7

| | Ingredients in Foaming Formulation (wt %) | | | Results (0.20% Solution of the Formulations) | | |
|---|---|---|---|---|---|---|
| Sample | B-PRV | Water | Foam Boosting Blend | Initial Foam Volume (ml) | Foam Volume at 5 minutes (ml) | % Foam Loss between 0 and 5 minutes |
| 04-339 Samples | | | | | | |
| 04-339A | 50 | 50 | 0 | 150 | 140 | 6.67% |
| 04-339A | 50 | 50 | 0 | 150 | 140 | 6.67% |
| 04-339B | 50 | 49 | 1 | 170 | 170 | 0.00% |
| 04-339B | 50 | 49 | 1 | 165 | 165 | 0.00% |
| 04-339C | 50 | 47 | 3 | 170 | 170 | 0.00% |
| 04-339C | 50 | 47 | 3 | 172 | 173 | −0.58% |
| 04-339D | 50 | 44 | 6 | 170 | 170 | 0.00% |
| 04-339D | 50 | 44 | 6 | 175 | 175 | 0.00% |
| 04-339E | 50 | 42 | 8 | 170 | 170 | 0.00% |
| 04-339E | 50 | 42 | 8 | 170 | 170 | 0.00% |
| 04-339F | 50 | 40 | 10 | 150 | 140 | 6.67% |
| 04-339F | 50 | 40 | 10 | 140 | 135 | 3.57% |
| 04-353 Samples | | | | | | |
| 04-353A | 50 | 50 | 0 | 150 | 140 | 6.67% |
| 04-353A | 50 | 50 | 0 | 152 | 140 | 7.89% |
| 04-353B | 50 | 47 | 3 | 170 | 170 | 0.00% |
| 04-353B | 50 | 47 | 3 | 175 | 174 | 0.57% |
| 04-353C | 50 | 45 | 5 | 172 | 173 | −0.58% |
| 04-353C | 50 | 45 | 5 | 170 | 170 | 0.00% |
| 04-353D | 50 | 42 | 8 | 162 | 163 | −0.62% |
| 04-353D | 50 | 42 | 8 | 160 | 158 | 1.25% |
| 04-353E | 50 | 38 | 12 | 158 | 155 | 1.90% |
| 04-353E | 50 | 38 | 12 | 160 | 155 | 3.13% |
| 04-353F | 50 | 35 | 15 | 140 | 135 | 3.57% |
| 04-353F | 50 | 35 | 15 | 145 | 140 | 3.45% |

Example 5

Clinical Testing of a Hand Soap Having the Foam Boosting Blend

Figure 3:
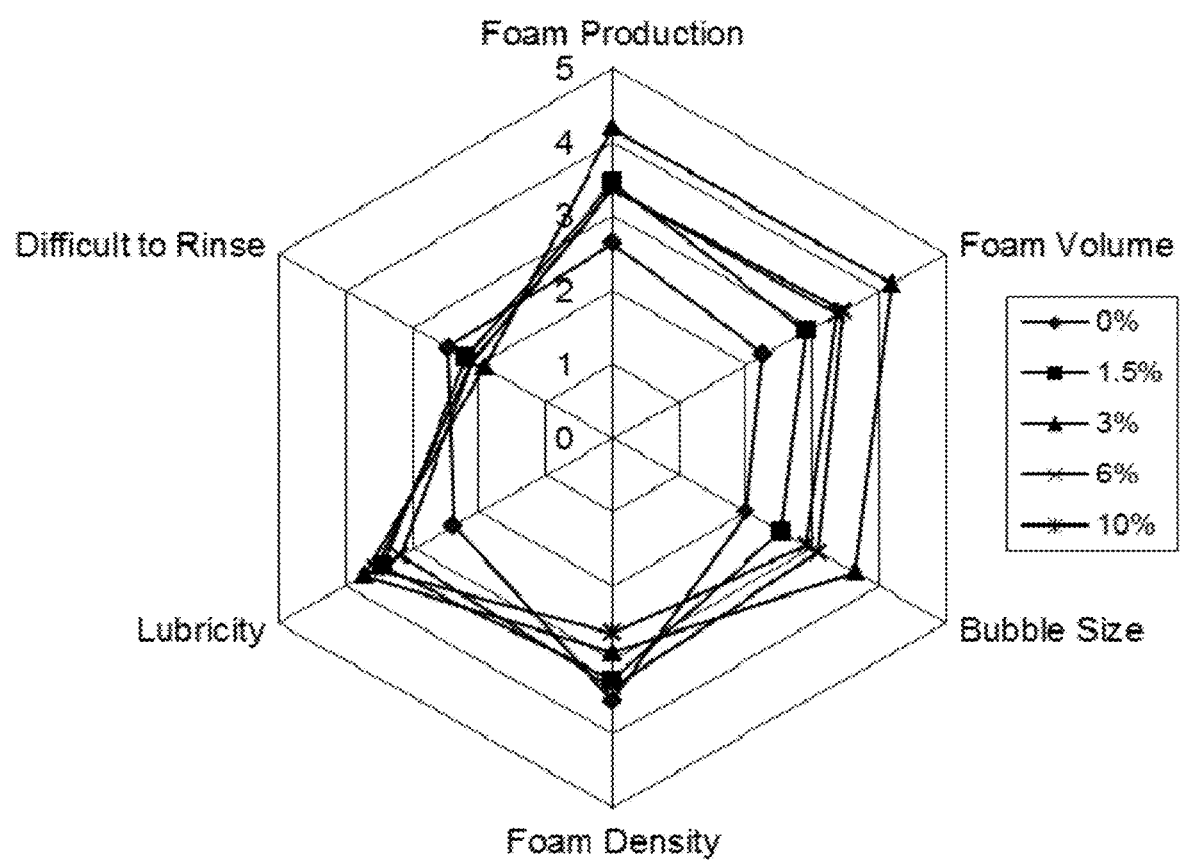
FIG. 3—Shows the averages of clinical evaluations for hand soap formulations containing 0%, 1.5%, 3%, 6%, and 10% foam booster blend (n=11). Volunteers evaluated each formulation for foam production, foam volume, bubble size, foam density, lubricity, and difficulty to rinse. The foam boosting blend provides a noticeable increase in favorability for foam production, foam volume, bubble size, and lubricity.

Foam boosting blend was added to a hand soap formulation based on the ingredient list described in Table 8 by adding the foam boosting blend at different concentrations into the formula via mixing and adjusting the water to account for the boosting blend (i.e., q.s down with water) (see Table 8 for Formulations A through E with differing foam boosting blend concentrations from 0% to 10% by weight). Eleven volunteers were asked to rate Formulations A through E for their favorability of the formulation's ability to produce foam, the foam volume produced, the bubble size produced, the lubricity of the formulation, the foam density produced, and the difficulty to rinse off the formulation. Volunteers rated each composition independently using a scale of 1 to 5, 1 representing "least favorable" and 5 representing "most favorable." The volunteers were not told what each formulation contained and were not allowed to discuss their results with the other volunteers. The addition of the foam boosting blend at multiple concentrations provided a noticeable increase in favorability for foam production, foam volume, bubble size, and lubricity when compared to Formulation A, which contained no foam boosting blend (See Table 9 and FIG. 3).

TABLE 8*

| | % Concentration (by weight) in Each Formula | | | | |
|---|---|---|---|---|---|
| | A | B | C | D | E |
| Ingredients in Order of Addition | | | | | |
| 1. Water | 46.95 | 45.45 | 43.95 | 40.95 | 36.95 |
| 2. Acrylates Copolymer (Synthalen W400) | 10.00 | 10.00 | 10.00 | 10.00 | 10.00 |
| 3. Cocamidopropyl Betaine | 30.00 | 30.00 | 30.00 | 30.00 | 30.00 |
| 4. Lauryl Glucoside (Endinol Mild LG-1250) | 10.00 | 10.00 | 10.00 | 10.00 | 10.00 |
| 5. Sodium Hydroxide 50% | q.s. | q.s. | q.s. | q.s. | q.s. |
| 6. Olive Oil Glycereth-8 Esters (Olivatis 15) | 2.00 | 2.00 | 2.00 | 2.00 | 2.00 |
| 6. Foam Boosting Blend | 0.00 | 1.50 | 3.00 | 6.00 | 10.00 |
| 7. Fragrance | 1.00 | 1.00 | 1.00 | 1.00 | 1.00 |
| 7. Methylchloroisothiazolinone/methylisothiazolinone (Sharomix MCI II) | 0.05 | 0.05 | 0.05 | 0.05 | 0.05 |
| Properties of the Formulations | | | | | |
| Viscosity (cps) | 4090 | 5333 | 5600 | 5407 | 5620 |
| pH (10%) | 5.5 | 5.82 | 6.05 | 6.1 | 6.02 |

*The appearance of the formulations were clear water white to pale yellow liquid

TABLE 9

| | Average Rating (1-5 Scale) for Each Formulation | | | | |
|---|---|---|---|---|---|
| Test | A | B | C | D | E |
| Foam Production | 2.64 | 3.45 | 4.18 | 3.36 | 3.36 |
| Foam Volume | 2.27 | 2.91 | 4.18 | 3.45 | 3.36 |
| Bubble Size | 2.00 | 2.55 | 3.64 | 3.09 | 2.91 |
| Foam Density | 3.55 | 3.27 | 2.91 | 3.36 | 2.64 |
| Lubricity | 2.36 | 3.45 | 3.73 | 3.18 | 3.55 |
| Difficulty to Rinse | 2.45 | 2.18 | 1.91 | 2.09 | 2.09 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A foamable liquid cleansing composition comprising:
   a foam booster comprising a saccharide blend having:
   (a) 30 wt. % to 50 wt. % of an aldohexose or mixture of aldohexoses;
   (b) 20 wt. % to 55 wt. % of a ketohexose or mixture of ketohexoses; and
   (c) 10 wt. % to 25 wt. % of a disaccharide or mixture of disaccharides; and
   a foaming detergent or surfactant,
   wherein the composition is configured to foam and cleanse skin and/or hair.

2. The composition of claim 1, wherein the foam booster comprises:
   (a) 35 wt. % to 45 wt. % of an aldohexose or mixture of aldohexoses;
   (b) 25 wt. % to 30 wt. % of a ketohexose or mixture of ketohexoses; and
   (c) 12 wt. % to 20 wt. % of a disaccharide or mixture of disaccharides.

3. The composition of claim 1, wherein the aldohexose is glucose or dextrose, or a combination thereof, the ketohexose is fructose, and the disaccharide is maltose.

4. The composition of claim 1, wherein the foam booster further comprises 5 wt. % to 20 wt. % polysaccharides with at least 4 monosaccharide units.

5. The composition of claim 1, wherein the foam booster increases foaming power of the composition as characterized by a foam height increase greater than 10% measured according to a cylinder shake method for the composition as compared to the composition without the foam booster.

6. The composition of claim 1, wherein the composition is a shampoo, body wash, soap, and/or hand cleanser.

7. The composition of claim 1, comprising 1 wt. % to 8 wt. % of the foam booster.

8. The composition of claim 1, wherein the composition is a body wash, soap, and/or hand cleanser.

9. The composition of claim 1, further comprising a fragrance.

10. The composition of claim 1, wherein the composition is a shampoo.

11. The composition of claim 1, wherein the composition has a pH of 3 to 11.

12. A method of cleansing skin and/or hair, the method comprising topically applying the composition of claim 1 to skin and/or hair and then removing the composition from the skin and/or hair.

13. The method of claim 12, wherein the foam booster increases foaming power of the composition as characterized by a foam height increase greater than 10% measured according to a cylinder shake method for the composition having the foam booster as compared to the composition without the foam booster.

14. The method of claim 12, wherein the composition comprises 1 wt. % to 8 wt. % of the foam booster.

15. The method of claim 12, wherein the composition is applied to skin.

16. The method of claim 12, wherein the composition further comprises a fragrance.

17. The method of claim 12, wherein the composition is applied to hair.

18. The method of claim 12, wherein the composition is a shampoo.

19. The method of claim 12, wherein the composition is a body wash, soap, and/or hand cleanser.

* * * * *